(12) United States Patent
Jarvinen

(10) Patent No.: US 6,190,378 B1
(45) Date of Patent: Feb. 20, 2001

(54) CRYOSURGICAL INSTRUMENT AND RELATED TECHNIQUES

(75) Inventor: Philip O. Jarvinen, Amherst, NH (US)

(73) Assignee: Massachusetts Institute of Technology, Cambridge, MA (US)

( * ) Notice: Under 35 U.S.C. 154(b), the term of this patent shall be extended for 0 days.

(21) Appl. No.: 09/193,497

(22) Filed: Nov. 16, 1998

Related U.S. Application Data (60) Provisional application No. 60/067,606, filed on Dec. 5, 1997.

(51) Int. Cl.$^7$ ............................................. A61B 17/36
(52) U.S. Cl. ............................ 606/21; 606/20; 606/23
(58) Field of Search ................................... 606/20–26

(56) References Cited

U.S. PATENT DOCUMENTS

| | | | |
|---|---|---|---|
| 3,663,917 | 5/1972 | Mahmoodi | 338/28 |
| 3,678,751 | 7/1972 | Mead et al. | 73/362 |
| 3,866,472 | 2/1975 | Witt | 73/362 |
| 4,058,787 | 11/1977 | Ichikawa et al. | 338/22 |
| 4,140,109 | 2/1979 | Savic et al. | 128/2.1 |
| 4,166,389 | 9/1979 | Montren | 73/343 |
| 4,252,130 | 2/1981 | LePivert | 128/734 |
| 4,437,084 | 3/1984 | Clayton, Jr. | 338/22 |
| 4,453,835 | 6/1984 | Clawson et al. | 374/185 |
| 4,457,633 | 7/1984 | Andrews | 374/209 |
| 5,647,868 * | 7/1997 | Chinn | 606/21 |
| 5,800,487 * | 9/1998 | Mikus et al. | 607/105 |
| 5,899,897 * | 5/1999 | Rabin et al. | 606/21 |
| 5,899,899 * | 5/1999 | Arless et al. | 606/22 |
| 5,906,612 * | 5/1999 | Chinn | 606/20 |

FOREIGN PATENT DOCUMENTS

| | | |
|---|---|---|
| 0400157 | 7/1984 | (EP) . |
| 0494834 | 1/1992 | (EP) . |
| 1532868 | 12/1989 | (RU) . |

OTHER PUBLICATIONS

H. Arkin, L. X. Xu and K.R. Holmes, Recent Developments in Modeling Heat Transfer in Blood Perfused Tissues, IEEE Transactions on Biomedical Engineering, vol. 41, No. 2, Feb. 1994, pp. 97–107.

D. K. Bahn, et al. Prostate Cancer: US–guided Percutaneous Cryoablation, Radiology, 194:551–556, 1995.

H.S. Carslaw and J.C. Jaeger, Conduction of Heat in Solids, Oxford at the Clarendon Press, second edition, undated, pp. 210–213.

T. E. Cooper and G.J. Trezek, Analytical Prediction of the Temperature Field Emanating from a Cryogenic Surgical Cannula, Cryobiology, vol. 7, No. 2–3, 1970, pp. 79–93.

(List continued on next page.)

*Primary Examiner*—Linda C. M. Dvorak
*Assistant Examiner*—David M. Ruddy
(74) *Attorney, Agent, or Firm*—Daly, Crowley & Mofford, LLP (57) ABSTRACT

A cryosurgical instrument includes a cryoprobe operative to form an ice ball in tissue of a patient targeted for cryosurgery upon activation, a sheath disposed over the cryoprobe and at least one measuring device supported by the sheath for measuring a parameter of the tissue of the patient. The instrument includes a processor for predicting formation of the ice ball by the cryoprobe over time and a display for displaying the prediction of ice ball formation. The processor is responsive to an output signal provided by the measuring device and a model of the effective thermal conductivity of the tissue of the patient targeted for surgery. In one embodiment, the measuring device is embedded in the sheath and measures temperature, thermal conductivity, blood perfusion rate and/or thermal diffusivity. The processor may be further responsive to an impedance measurement circuit for verifying the prediction.

26 Claims, 7 Drawing Sheets

OTHER PUBLICATIONS

G. Delhomme, W. H. Newman, B. Roussel, M. Jouvet, H. Frederik Bowman and A. Dittmar, Thermal Diffusion Probe and Instrument System for Tissue Blood Flow Measurements: Validation in Phantoms and In Vivo Organs, IEEE Transactions on Biomedical Engineering, vol. 41, No. 7, Jul. 1994, pp. 656–661.

M. B. Garnick, The Dilemmas of Prostate Cancer, Scientific America, Apr. 1994, pp. 72–81.

F. L. Lee, et al., US–guided Percutaneous Cryoablation of Prostate Cancer, Radiology 192, 1994, pp. 769–776.

I. c. Martin and R. Holanda, Applications of Thin Film Thermocouples for Surface Temperature Measurement, NASA Technical Memorandum 106714, Jul. 24, 1994, pp. 1–13.

S. J. Novak and D. L. Craig, A Low–Cost Impedance Based Cryosurgical Temperature Measurement Unit, Australasian Physical & Engineering Sciences in Medicine (1984) vol. 7, No. 3.

P.C. Walsh and J.F. Worthington, The Prostate—A Guide for Men and Women who Love them, The John Hopkins University Press, 1995.

J.W. Valvano, J.T. Allen, and H. F. Bowman, The Simultaneous Measurement of Thermal Conductivity, Thermal Diffusivity, and Perfusion in Small Volumes of Tissue, Journal of Biomechanical Engineering, vol. 106, Aug. 1984, pp. 192–197.

W. B. Bald, A Helium Gas Probe for Use in Cryosurgery, Cryobiology, 21, 1984, pp. 570–573.

D. Bendesky, A Special Thermocouple for Measuring Transient Temperatures, Mechanical Engineering, Feb. 1953, pp. 117–121.

H. Budman, et al. Investigation of Temperature Fields around Embedded Cryoprobes, Transactions of the ASME, 108, 1986, pp. 42–48.

Z. Chang, Development of a High–Performance Multiprobe Cryosurgical Device, Biomedical Instrumentation & Technology, Sep./Oct. 1994, pp. 383–390.

M. Garnick, The Dilemmas of Prostate Cancer, Scientific American, Apr. 1994, pp. 72–76, 78, 80 and 81.

S. A. Haider, Temperature Distribution in Tissue from a Regular Array of Hot Source Implants: An Analytical Approximation, IEEE Transactions on Biomedical Engineering, 40, 5, May 1993, pp. 408–417.

J. P. Homasson, et al., The Operation and Efficacy of Cryosurgical, Nitrous Oxide Driven Cryoprobe, Cryobiology, 31, 1994, pp. 290–304.

P. Le Pivert, Measurement of Intratissue Bioelectrical Low Frequency Impedance: A New Method to Predict Per–Operatively the Destructive Effect of Cryosurgery, Crybiology, vol. 14, 245–250 (1977).

P. J. LePivert, The Measurement of Low Frequency Electrical Impedance as a Guide to Effective Cryosurgery, J. Dermatol. Surg. Oncol., 3:4, 1977, pp. 395–396.

G. Onik, et al., Transrectal Ultrasound–Guided Percutaneous Radical Cryosurgical Ablation of the Prostate, Cancer, Aug. 15, 1992, vol. 72, No. 4, 1291–1299.

H. H. Pennes, Analysis of Tissue and Arterial Blood Temperatures in Resting Forearm, Journal Of Applied Physiology, 1, 1948, pp. 93–122.

M. Reiser, et al., The use of CT in Monitoring Cryosurgery, European Journal of Radiology, vol. 3, 1983, pp. 123–128.

J. Valvano, The Use of Thermal Diffusivity to quantify Tissue Perfusion, Massachusetts Institute of Technology Thesis, Aug. 1981, 13 pages.

* cited by examiner

CRYOSURGICAL INSTRUMENT AND RELATED TECHNIQUES

CROSS-REFERENCE TO RELATED APPLICATIONS

This application claims priority under 35 U.S.C. §119(e) to U.S. Provisional Application No. 60/067,606 filed Dec. 5, 1997.

STATEMENTS REGARDING FEDERALLY SPONSORED RESEARCH

This invention was made with government support under Contract Number F19628-95-C-0002 awarded by the United States Air Force. The government has certain rights in the invention.

BACKGROUND OF THE INVENTION

Cryosurgery, a surgical procedure in which a target area of a patient is frozen, is known for treating various medical conditions. Most often, cryosurgery is used in the treatment of cancer, in which a cancerous mass or tumor is destroyed during the freezing process. Over time, the frozen mass deteriorates and is consumed by the body. One application for cryosurgery is in the treatment of prostate cancer.

Prostate cancer is one of the most frequently diagnosed malignancies in American males and is the second leading cause of cancer related deaths. Successful treatment requires confining the cancer to the prostate gland and surrounding tissue, referred to as the prostatic capsule, in order to prevent the spread and metastasizing of the cancer.

In addition to cryosurgery, other conventional treatment therapies for prostate cancer include radical prostatectomy, radiation therapy and medical or surgical castration. In radical prostatectomy, the prostate gland and a margin of the surrounding tissue are surgically removed. However, a relatively high rate of recurrent, or residual tumors have been reported following radical prostatectomy. Further, this form of treatment suffers from a relatively high rate of impotence and/or incontinence.

In radiation therapy, radiation is applied to the prostate gland either by an external source or by radioactive implants. However, in many reported cases, the ability of radiation therapy to control cancer has been found to last only a few years.

Medical castration involves the administering of drugs that shut down a bodily process, such as the production of testosterone or the effect of testosterone on the prostate gland. This form of therapy does not cure the cancer and, over time, the cancer usually progresses. Surgical castration does not appear to be any more effective than medical castration and both types of castration can cause hot flashes, loss of sex drive, enlargement of the breasts and impotence.

Prostate cryosurgery involves the use of multiple liquid nitrogen or gas cooled probes (i.e., cryoprobes) inserted into the prostate through the perineum to freeze the prostate gland, thereby killing the cancer. Typically, five cryoprobes are used and the frozen area around each cryoprobe is sometimes referred to as an "ice ball." An ultrasound probe is used to guide the cryoprobes into position in the prostate and to permit the physician to visualize the edge of the ice balls or the overall ice ball formed by the cryoprobes. Temperature sensing thermocouples are positioned external to the prostatic capsule to measure the surrounding temperatures.

By visualizing the edge of the ice balls and monitoring the temperature adjacent to the prostate gland, the physician controls activation of the cryoprobes in an effort to ensure that the entire cancerous area is frozen and further, to ensure that adjacent areas are not frozen in order to prevent certain side effects. In particular, freezing nerves adjacent to prostate or the seminal vesicle can cause impotence and freezing the urethra, bladder or the rectal sphincter muscle can cause incontinence problems. During the cryosurgical procedure, generally, a warm fluid is directed through the urethra which passes through the prostate gland in order to help prevent freezing of the urethra.

Since ultrasound provides a two-dimensional image, only the edge of the ice balls can be visualized and thus, the physician is not provided with any information regarding temperatures behind the ice ball edge. Further, the edge of the ice ball is at approximately 0° C. and, in order to effectively destroy cancer, the tissue must be frozen to temperatures between approximately −20° C. and −40° C. Thus, the physician must estimate what portion of the ice ball has effectively destroyed the cancer. This task is complicated by the fact that ice ball formation is dependent on certain physiological parameters of the patient, such as blood flow and tissue properties.

Although prostate cryosurgery has not been in use as long as the other prostate cancer treatment therapies, it has displayed nearly an eighty-percent success rate in destroying prostate cancer. Further, prostate cryosurgery has the advantage that patients usually do not suffer serious urinary control problems. However, the success of prostate cryosurgery in destroying cancer without causing impotence and other side effects is dependent on the precision with which the entire cancerous area and no additional area is frozen.

BRIEF SUMMARY OF THE INVENTION

The invention relates to a cryosurgical instrument including at least one, and preferably a plurality of cryoprobes adapted for being positioned in tissue of a patient targeted for cryosurgery, such as the prostate gland, and operative to form an ice ball in the tissue upon activation. Each of the cryoprobes has a sheath disposed over at least a portion thereof which supports at least one measuring device for measuring a parameter of the tissue of the patient. Preferably, the measuring device is embedded in the sheath and measures tissue temperature, thermal conductivity, blood perfusion rate and/or thermal diffusivity. In one embodiment, the sheath includes a plurality of measuring devices embedded therein and spaced along a portion of the sheath both axially and longitudinally.

The instrument further includes a processor for predicting formation of an ice ball by each of the cryoprobes in the tissue over time and a display for displaying the ice ball formation prediction. More particularly, the processor is responsive to an output signal of the measuring device indicative of a measurement performed prior to cryosurgery for providing the ice ball formation prediction. The processor is further responsive to a model of the thermal properties of the tissue of the patient and to the effect of urethral warming. The display provides a representation of the temperature contours within the prostate gland that would result from activation of the cryoprobes. With this arrangement, a physician is able to perform "trial" cryosurgical procedures without activating the cryoprobes in order to determine an optimum treatment procedure.

In one embodiment, the measuring device is further operative to measure a parameter of the tissue following activation of the cryoprobes (i.e., during cryosurgery). The processor is responsive to this "surgery" measurement for verifying the ice ball formation prediction. The cryosurgical instrument may further include an impedance measurement circuit coupled to selected ones of the cryoprobes for providing an output signal indicative of the tissue impedance with which the ice ball formation prediction is verified.

Also provided is a method of predicting ice ball formation by one or more cryoprobes in tissue of a patient targeted for cryosurgery including the steps of forming a model of the thermal properties of the tissue of the patient and measuring at least one parameter associated with the tissue of the patient prior to activation of the cryoprobes. The method further includes predicting the formation of the ice balls by the cryoprobes in the tissue of the patient in response to the model and the measured parameter. The method may further include the step of measuring a tissue parameter following activation of the cryoprobes and verifying the ice ball formation prediction based on this "surgery" measurement. Further optional steps include measuring the impedance of the tissue and verifying the ice ball formation prediction based on the measured impedance.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
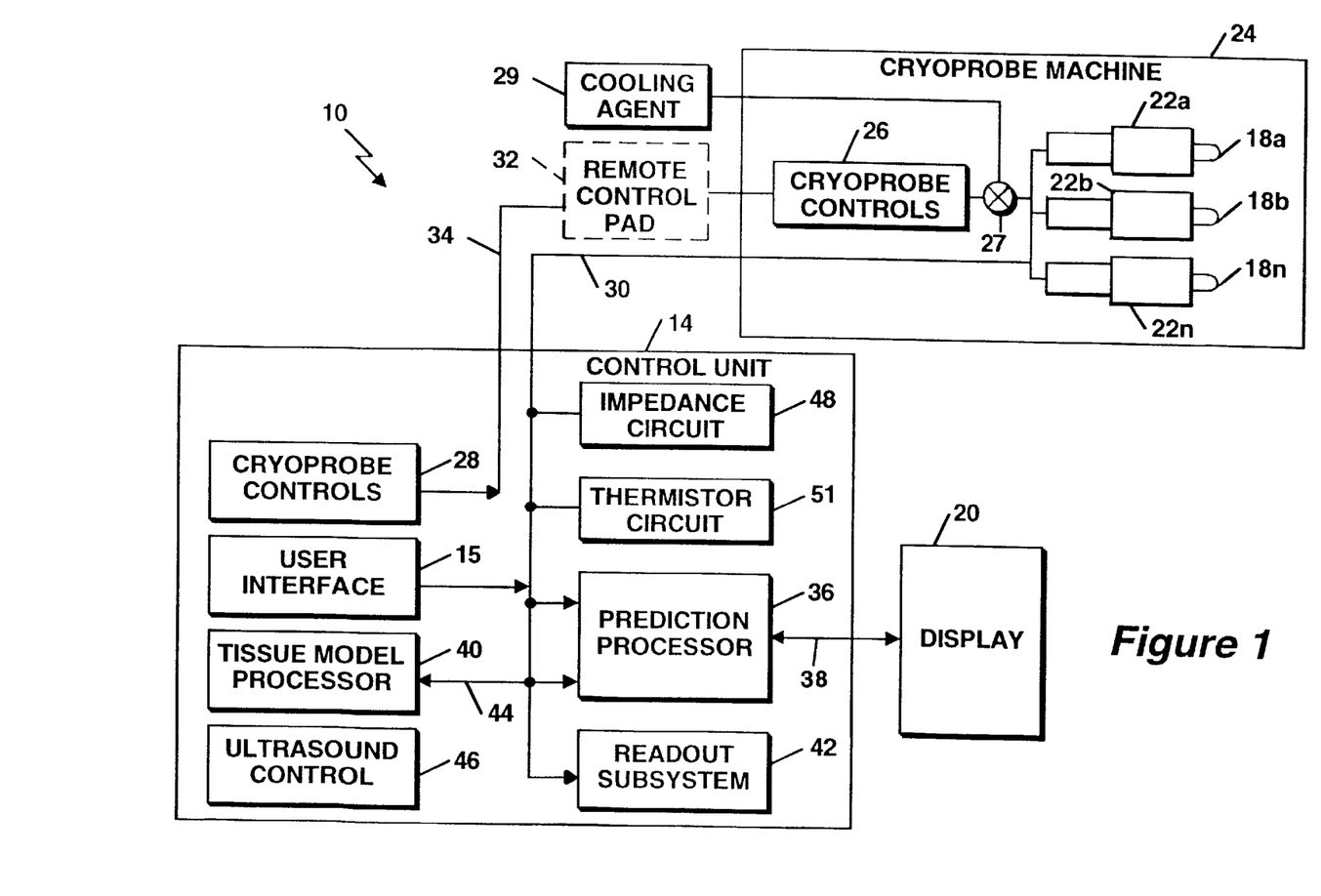
FIG. 1 is a block diagram of a cryosurgical instrument according to the invention.

Referring to FIG. 1, a cryosurgical instrument, or system 10 according to the invention includes a control unit 14, a display 20 and a cryoprobe machine 24 including a plurality of cryoprobes 18a, 18b, . . . 18n. The cryoprobes 18a–18n are adapted for insertion into tissue of a patient targeted for cryosurgery. Upon activation, each cryoprobe 18a–18n freezes surrounding tissue so as to form an "ice ball". Generally, the cryoprobes 18a–18n are positioned such that individual ice balls formed by the cryoprobes 18a–18n overlap to form a cumulative ice ball. Over time, the ice balls deteriorate and are consumed by the body.

The illustrative cryosurgical system 10 is particularly well-suited for prostate cryosurgery and will be described with specific reference to that application. It will be appreciated by those of ordinary skill in the art however, that the apparatus and techniques described herein are suitable for use in other cryosurgical applications.

The cryoprobes 18a–18n are elongated, partially hollow tubular devices, each having a sheath 22a, 22b, . . . 22n covering at least a portion thereof in use. The probes 18a–18n are cooled by a cooling agent, such as liquid nitrogen, nitrogen oxide gas or carbon dioxide gas, which is circulated through the cryoprobe. Typically, the cryoprobe machine 24 includes five cryoprobes. In accordance with one feature of the invention, each of the sheaths 22a–22n includes at least one measuring device 80a–80h (FIG. 3), such as a thermistor, for measuring a parameter of the tissue of the patient and for providing a parameter output signal to the control unit 14 via measurement connections 30, as will be described.

In the illustrative embodiment, the control unit 14 includes cryoprobe controls 28 coupled to the cryoprobe machine 24 via control connections 34 for controlling the operation of the cryoprobes 18a–18n. As examples, the controls 28 govern activation, de-activation, and the amount of cooling agent delivered to the cryoprobes 18a–18n (i.e., the operating temperature of the cryoprobes). The controls 28 may replicate controls 26 on the cryoprobe machine 24, in which case the cryoprobe machine 24 includes a remote control pad 32 abutting the controls 26. With this arrangement, when a control 28 on the control unit 14 is actuated, a signal is transmitted to the remote control pad 32 which energizes an electromechanical plunger, causing the plunger to press down against and actuate the corresponding one of the cryoprobe controls 26 on the cryoprobe machine 24. Alternatively, the controls 26 on the cryoprobe machine 24 may be connected directly to the controls 28 on the control unit 14, thereby eliminating the need for the remote control pad 32. As a further alternative, the cryoprobe controls 28 on the control unit 14 may be eliminated and cryoprobe control effected by actuation of the controls 26 on the cryoprobe machine 24. This arrangement would require the time of activation and de-activation of each cryoprobe 18a–18n as well as the operating temperature of the cryoprobes to be manually entered into the control unit 14 via a user interface 15, such as a keyboard, for use as described below.

The cooling agent may be housed in a unit 29 disposed in, or proximal to the cryoprobe machine 24, as shown. In this case, a valve 27 coupled between the controls 26 and the cryoprobes 18a–18n controls the flow of cooling agent to and from the probes in response to actuation of the controls 28 of the control unit 14. Various types of valves, including proportional valves and on/off pulsed valves, are suitable for this purpose. Alternatively, the cooling agent unit 29 and valve 27 may be located in, or proximal to, the control unit 14, in which case the control connections 34 between the cryoprobe controls 28 on the control unit 14 and the cryoprobe controls 26 on the cryoprobe machine 24 include tubing for carrying the cooling agent to and from the probes 18a–18n.

As will become apparent, it is contemplated that the cryosurgical system 10 be used in conjunction with ultrasound equipment, including an ultrasound probe 60 (FIG. 2) and associated controls, to facilitate placement of the probes 18a–18n in the targeted tissue. Ultrasound controls 46 may be incorporated into the control unit 14 as shown in FIG. 1 or, alternatively, may be provided as part of a separate unit (not shown).

A prediction processor 36 predicts the formation of ice balls in the tissue of a patient targeted for cryosurgery by each of the cryoprobes 18a–18n prior to the cryosurgical procedure. The processor 36 is responsive to the tissue parameter, or parameters measured by the measuring devices 80a–80h associated with the probe sheaths 22a–22n (FIG. 3) and to a model of thermal characteristics of the treated tissue, such as thermal conductivity (i.e., a "global tissue model"). To this end, a tissue model processor 40 generates the global tissue model in response to measured tissue parameters and to certain treatment parameters entered by the operator of the apparatus and provides the global tissue model to the prediction processor 36 via connection 44.

It will be appreciated by those of ordinary skill in the art, that the prediction processor 36 and tissue model processor 40 may be implemented using various software executable on various hardware, such as an INTEL-compatible microprocessor of a standard personal computer. In the illustrative embodiment, the prediction processor 36 is implemented with a commercially available heat transfer computer program entitled Systems Improved Numerical Differencing Analyzer (SINDA) sold by Network Analysis, Inc. of Tempe, Ariz. and the tissue model processor 40 is implemented with software compatible with SINDA, since the global tissue model provides an input to the SINDA program.

The control unit 14 further includes a thermistor circuit 51 for permitting measurements to be made by thermistor measuring devices 80$a$–80$h$ (FIG. 3) associated with the sheaths 22$a$–22$n$, including temperature, thermal conductivity, blood perfusion rate and thermal diffusivity, as will be described further below. A product including such a thermistor circuit 51 is commercially available from Thermal Technologies of Cambridge, Mass. In general, the thermistor circuit 51 applies electrical energy to the thermistors to elevate their temperature relative to the surrounding tissue by a predetermined amount. The amount of applied electrical energy is measured and used to compute effective tissue thermal conductivity and, optionally, also blood perfusion rate and thermal diffusivity. Temperature is measured with the thermistors 80$a$ –80$h$ by passing a known current through the thermistors and measuring the resulting voltage drop.

Also provided in the control unit 14 is an optional impedance circuit 48 for measuring the impedance of the treated tissue. When measuring impedance, the impedance circuit 48 introduces an alternating current (AC) voltage to two of the cryoprobes 18$a$–18$n$, one of which is located at a measurement site and the other of which serves as a reference probe located at a reference site (both probes being referred to collectively as the measurement probes). Alternatively, a separate reference probe, not operative to freeze tissue, may be provided for insertion into the patient. Suitable reference probes include gold-plated or stainless steel rod-type electrodes. While it is contemplated that the impedance circuit 48 permits both the frequency and magnitude of the applied AC voltage to be varied, preferably, the AC voltage has a nominal frequency on the order of 1 KHz. It is further contemplated that the spacing between the impedance measurement probes be on the order of between 0.25 and 1.5 inches.

Since the voltage applied to the measurement probe by the impedance circuit 48 is known, a readout of the current passing between the probes provides an indication of the tissue impedance therebetween. The impedance circuit 48 may be a "self-contained" unit which permits readout of the impedance measurements in addition to applying the AC voltage to the measurement probes, such as the type sold by Hewlett-Packard as the 4263B LCR meter or the 4192A LF impedance analyzer. Alternatively, the impedance circuit 48 may serve only to apply the AC voltage to the measurement probes and the impedance measurement readout may be performed by a readout subsystem 42 of the control unit 14.

The prediction processor 36 is coupled to the display 20 via connection 38, as shown. The ice ball formation prediction provided by the processor 36 is displayed on the display 20, as described further in conjunction with FIG. 8. With this arrangement, a physician can perform "trial" cryosurgical procedures, prior to surgery, during which the physician is able to observe predicted ice ball formation prior to activation of the cryoprobes. This information is useful to determine and implement an optimum cryosurgical treatment procedure. Further, during cryosurgery, the physician is able to visualize ice ball formation and, in particular, temperature contours within and around the treated tissue in real time, as the ice ball is being formed.

It will be appreciated that the particular arrangement and grouping of system components in FIG. 1 is illustrative only and can be varied in many instances. For example, components of the control unit 14 may be housed together, or in one or more separate units. As one example, the components of the control unit 14, including the cryoprobe controls 28, ultrasound controls 46, impedance circuit 48, readout subsystem 42 and a computer on which the prediction processor 36 and tissue model processor 40 are implemented, are housed in a single hardware rack or enclosed housing. Alternatively, many or all of the components of the control unit 14 may be implemented in the chassis of a standard personal computer modified to receive the control unit components such as the cryoprobe controls 28, ultrasound controls 46, impedance circuit 48, thermistor circuit 51 and readout subsystem 42, which may be implemented on printed circuit boards adapted to plug into input/output slots of the computer chassis.

Figure 2:
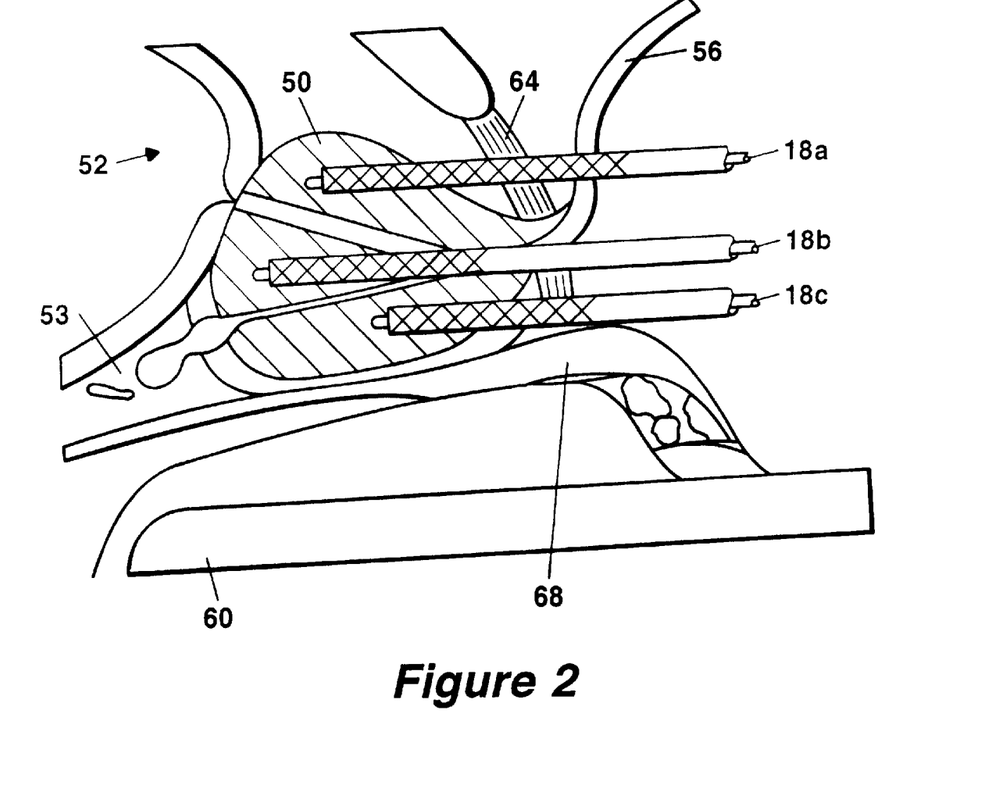
FIG. 2 shows the anatomy of a male patient.

Referring to FIG. 2, an illustrative prostate treatment region is shown to have three cryoprobes 18$a$, 18$b$ and 18$c$ inserted therein, for simplicity of illustration. The prostate gland 50 is a muscular, walnut size gland positioned directly behind the bladder 52. The urethra 56 passes through the prostate gland 50. Also shown in FIG. 2 is an ultrasound probe 60 disposed in the rectum. The ultrasound probe 60 is used to guide the cryoprobes 18$a$–18$c$ through the perineum 64 and into the prostate gland 50.

The importance of precision in freezing the prostate gland 50 so as to avoid deleterious side effects is evident from consideration of the anatomy of the prostate region. While a warm fluid is, generally directed through the urethra 56 during cryosurgery in order to help prevent freezing the urethra, it is likewise desirable to avoid freezing the mouth of the bladder 52, the rectal sphincter muscle 68 and the seminal vesicle 53, all of which are located in close proximity to the prostate gland 50.

Figure 3:
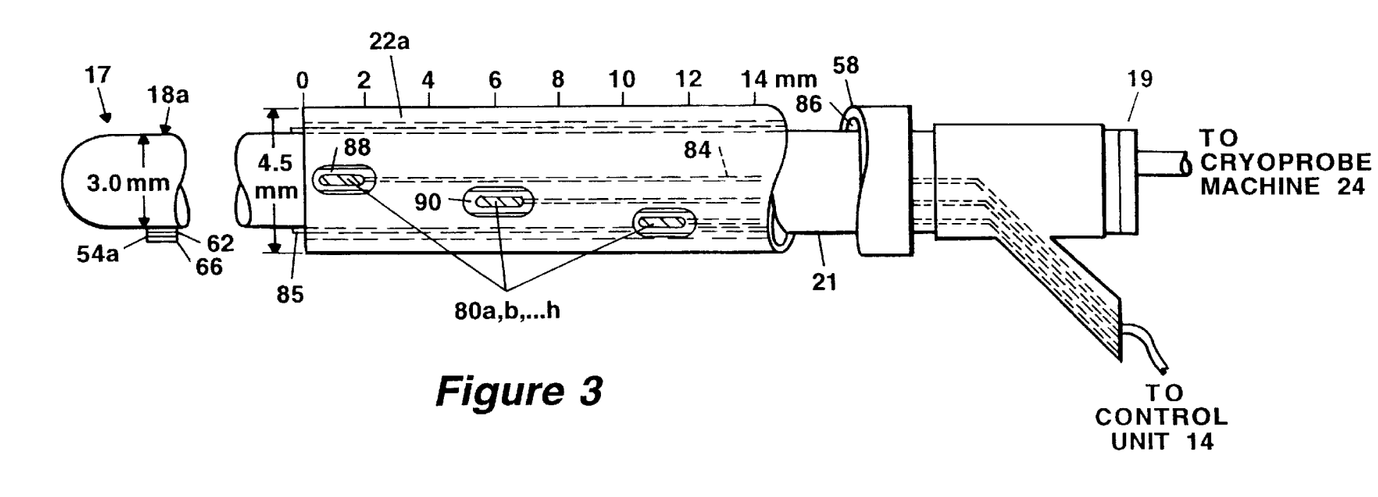
FIG. 3 is an enlarged partially cut-away view of a cryoprobe having a sheath according to the invention.

Referring also to FIG. 3, an enlarged view of an illustrative cryoprobe 18$a$ and sheath 22$a$ is shown. As noted above, the cryoprobe 18$a$ is an elongated, partially hollow tubular element through which a cooling agent, such as liquid nitrogen, is circulated. The cryoprobe 18$a$ may take various forms. As one example, the cryoprobe 18$a$ includes a relatively short, actively cooled tip portion 17 coupled to a longer metal tube 21 and then to a plastic tube which has a threaded fitting 19 adapted for attachment to the cryoprobe machine 24 (FIG. 1) and through which liquid nitrogen is routed to the probe tip 17. A central tube (not shown) within the probe which terminates adjacent to the tip is disposed concentrically within an outer return tube (not shown) also within the probe. The central tube carries the liquid nitrogen to the tip 17 and has a plurality of holes clustered at several locations along its length to allow nitrogen gas that may be produced to escape the central tube and return back to the cryoprobe machine 24 through the return tube. Any liquid nitrogen that reaches the tip 17 remains as liquid nitrogen or is vaporized and returns to the cryoprobe machine 24 via the return tube. Concentrically around the return tube is a vacuum tube (not shown) which is evacuated for insulating the probe. One such cryoprobe is commercially available from Cryomedical Sciences, Inc. of Rockville, Md. under the designation 3 mm×4 cm×18 cm blunt tip cryoprobe. The illustrative cryoprobe 18a has a diameter on the order of 3.0 mm and the actively cooled tip 17 is comprised of a suitable thermally conductive material, such as stainless steel, and has a length on the order of 4.0 cm.

Preferably, a layer of electrically insulating material 85 is disposed around at least a portion of the cryoprobe 18a. In the illustrative embodiment, a thin layer of insulating material, such as Teflon or aluminum oxide having a thickness on the order of a few microns, is disposed over a portion of the cryoprobe 18a starting at approximately an inch from the tip of the cryoprobe and extending back toward the fitting 19. Use of such an electrically insulating layer 85 advantageously improves the sensitivity of impedance measurements.

In the illustrative embodiment, at least one thermocouple 54 is mounted to at least one of the cryoprobes 18a–18n and, preferably, on each of the cryoprobes. More preferably, a plurality of thermocouples 54a–54k, such as five (only one of which, 54a, is shown), are disposed along a portion of each of the cryoprobes 18a–18n, such as along a 2.0 inch length longitudinally spaced by from the probe tip by 0.125 inches and from each other by 0.5 inches and rotationally spaced from each other by 72°. As will become apparent, temperature measurements provided by the thermocouples 54a–54k may be used to calibrate temperature measurements made with thermistor measuring devices 80a–80h supported by the sheath 22a and/or to provide probe temperature information for use by the prediction processor 36, as will be described. Since the change in resistance of thermistors increases significantly, into the Gigaohm range, as temperatures decrease below –150° C. and since the thermocouples 54a–54k are disposed on the probe 18a whereas the thermistors 80a–80h are disposed on the sheath 22a, it may be desirable to use the thermocouples 54a–54k to provide the probe temperature information for use by the prediction processor.

Preferably, the thermocouples 54a–54k are fabricated by a thin-film technique and include a first, electrically insulating layer 62 disposed over the outer surface of the probe 18a. A low-profile thermocouple junction 54a–54k having a thickness on the order of a few microns is disposed over the insulating layer 62. Suitable materials for the thermocouple junction include iron/constantan, chromel/alumel, copper/constantan, chromel/constantan, platinum/rhenium, platinum/rhodium, and tungsten/rhenium and suitable application techniques include sputtering steps, photoresist metallization steps or a combination of both techniques. Thereafter, another thin layer of electrically insulating material 66 is applied over the thermocouple junction 54a–54k in order to electrically insulate the thermocouple from the sheath 22a or tissue with which it may be in contact. Suitable electrically insulating layers 62, 66 are comprised of aluminum oxide, or silicon oxide, for instance, and have a thickness on the order of a few microns. Wires coupling the thermocouples 54a–54k to the control unit 14 (FIG. 1) may be fabricated according to the same thin-film technique as the thermocouples themselves and adapted for connection to standard instrumentation wires at pads disposed distal from the probe tip portion 17.

The sheath 22a is a hollow tubular element having open ends through which the cryoprobe 18a extends. Conventionally, a sheath is disposed over a portion of a cryoprobe for the purpose of facilitating insertion of the cryoprobe into tissue. More particularly, conventional insertion of cryoprobes is accomplished by first inserting a hollow needle in the desired tissue location. A wire having a hook at one end is directed through the hollow needle and the hook is anchored to the tissue. Thereafter, the needle is retracted and a series of dilators of increasing diameter are guided over the wire until the target tissue location has been dilated to a width suitable to accommodate the sheath. The sheath is then inserted into the dilator, following which the dilator is removed. Finally, the cryoprobe is inserted into the sheath and the sheath is at least partially retracted to expose a portion of the cryoprobe, such as on the order of one inch.

In accordance with the present invention, in addition to facilitating insertion of the respective cryoprobe 18a in the above-described manner, the sheath 22a supports at least one measuring device 80a–80h for measuring a parameter of the tissue for use in predicting ice ball formation. Examples of parameters measured by the device on the sheath 22a include, but are not limited to, temperature, effective thermal conductivity, thermal diffusivity and blood perfusion rate.

In the illustrative embodiment, the sheath 22a includes a plurality of parameter measuring devices 80a–80h in the form of thermistors. Preferably the sheath 22a has eight thermistors 80a–80h embedded therein and equally spaced longitudinally along the forward two inches of the sheath, adjacent to the tip portion 17 of the probe 18a. The thermistors are also equally spaced radially around the circumference of the sheath 22a. Thus, each thermistor is longitudinally spaced from another by 0.25 inches and radially by 45°.

It is desirable that the thermistors 80a–80h have only a few ohms of resistance at 25° C., that they be relatively low cost, that they have a low negative slope to changes in resistance with temperature down to cryogenic temperatures, that they be formed from a material which is easily heated by passing a current through it, and that they have side by side leads that can be easily welded to instrumentation wires 84. Suitable thermistors are glass-encapsulated devices of the type sold by Fenwal Electronics Incorporated of Milford, Mass. under the product numbers 112-202EAJ-B01 and 111-202CAK-B01 and having a diameter of 1.14 mm, a length of 2.28 mm, a resistance of 2000 ohms at 25° C. and side by side leads of 0.10 mm diameter and 9.5 mm length.

Various techniques for fabricating the sheath 22a and forms of the sheath are possible. One sheath 22a, illustrated in FIG. 3, includes an inner Teflon tube 86 having an inner diameter slightly larger than, but close to, the diameter of the probe 18a and a thickness on the order of 0.04–0.06 inches. The thermistors 80a–80h are positioned on the inner tube 86 at the desired locations and are held in place with epoxy or other suitable substance. Wires 84 extending from the thermistors are also held in place along the length of the inner tube 86 with epoxy. Preferably, a plurality of slots or grooves 90 are carved into the inner tube 86 at eight equally-spaced locations around the circumference of the tube and the thermistors 80a–80h are placed in the grooves. The grooves 90 are sized and shaped so that the thermistors 80a–80h extend partially above the grooves (i.e., above the outer surface of the inner tube 86 ). Typical widths for the grooves 96 are on the order of 0.015–0.060 inches and typical depths for the grooves are on the order of 0.008–0.030 inches, depending on the dimensions of the particular thermistors.

A second, outer tube 58 having an inner diameter slightly smaller than the outer diameter of the inner tube 86 is positioned over the inner tube 86 in an interference fit. One way of achieving the interference fit is by cooling the inner tube 86 while heating the outer tube 58. With this arrangement, the inner tube 86 contracts while the outer tube 58 expands, permitting the inner tube to be inserted into the outer tube. When temperature equilibrium is reached, the inner tube 86 expands and the outer tube 58 contracts, thereby providing an interference fit therebetween. Apertures 88 are cut through the outer tube 58 around each of the thermistors 80a–80h in order to expose the thermistors 80a–80h and thereby to enhance the thermal response time of the thermistors by allowing direct thermal contact with the tissue and eliminating any intermediate material and its associated temperature drop.

Figure 4:
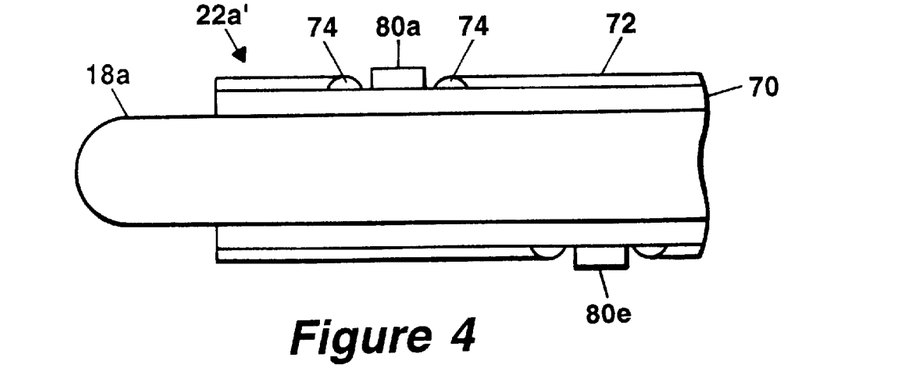
FIG. 4 is a cross-sectional view showing an alternate embodiment of the sheath of FIG. 3.

An alternative sheath 22a' is shown in FIG. 4 to include a relatively thin hollow Teflon tube 70 having a diameter slightly larger than the diameter of the probe 18a and a thickness on the order of 0.009–0.015 inches. The thermistors 80a–80h and wires 84 extending therefrom are arranged in the desired pattern on the outer surface of the tube 70 and are held in place with epoxy or are adhesively attached to a thin plastic sheet which is in turn adhesively attached to the outside of the thin Teflon tube 70. Thereafter, a thin Teflon shrink wrap layer 72 is applied over the tube 70 and the thermistors 80a–80h.

Once the shrink wrap layer 72 is applied, portions of the layer 72 covering the thermistors 80a–80h are removed, such as with a knife or heated tool. Cryogenic epoxy cement 74 is then applied to seal the edges of the shrink wrap layer 72 around each exposed thermistor 80a–80h. One way of applying the epoxy to these regions is with the use of a hypodermic syringe.

Figure 5:
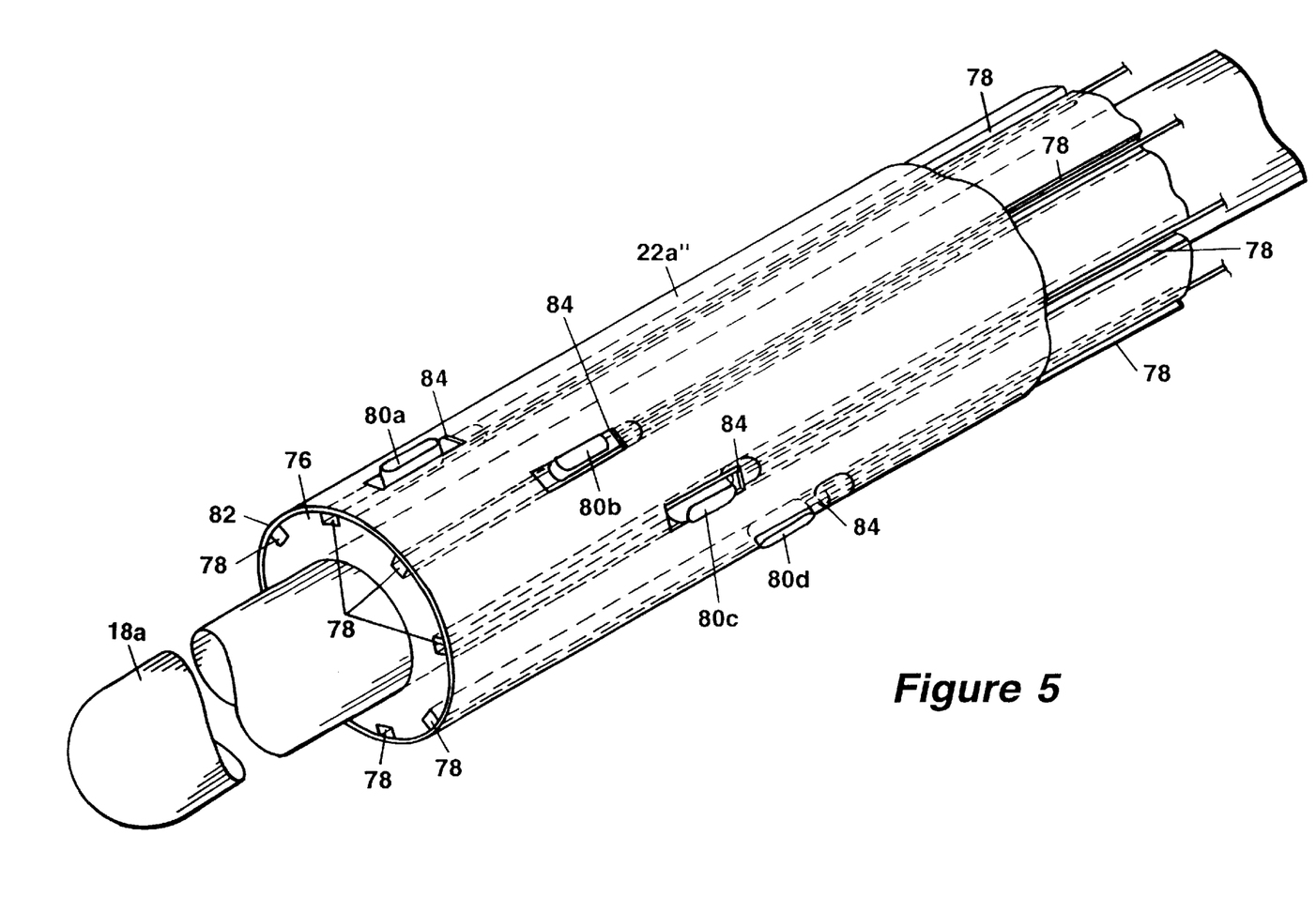
FIG. 5 is an isometric view showing an further alternate embodiment of the sheath of FIG. 3.

In an other alternative embodiment shown in FIG. 5, a sheath 22a" is comprised of a hollow Teflon tube 76, like tube 86 of FIG. 3, having a relatively thick wall, on the order of 0.040–0.060 inches. Slots, or grooves 78 are cut into the surface of the tube 76 along its length at eight equally spaced locations around the circumference of the tube. The width of the grooves 78 is selected to permit the thermistors 80a–80h to be seated therein and the depth of the grooves 78 is selected to ensure that the thermistors extend partially above the outer surface of the tube 76. In the illustrative embodiment, each groove 78 has a width on the order of approximately 0.015–0.060 inches and a depth on the order of approximately 0.008–0.030 inches.

A thin layer 82 of Teflon shrink wrap is then applied over the tube 76 and the thermistors 80a–80h. Thereafter, cryogenic epoxy cement 84 is inserted into the grooves 78 under the shrink wrap layer 82, such as with the use of a hypodermic syringe. Once the epoxy has set, portions of the shrink wrap layer 82 covering each of the thermistors 80a–80h are removed to expose the thermistors. In view of the various above-described sheath embodiments 22a, 22a' and 22a", it will be appreciated by those of ordinary skill in the art that various modifications and combinations of techniques are possible without departing from the spirit of the invention.

The thermistors 80a–80h supported by the sheath 22 a can be used to measure various parameters associated with the tissue, including tissue temperature, effective tissue thermal conductivity, blood perfusion rate, and thermal diffusivity, for use by the tissue model processor 40 and/or prediction processor 36. In order to measure tissue temperature, a known current is passed through the measuring thermistor by the thermistor circuit 51 and the resulting voltage drop across the thermistor is measured. The thermistor voltage drop can be compared to a thermistor calibration curve or against a temperature measurement made by one or more of the thermocouples 54a–54k, in order to convert the voltage drop into a temperature reading. Various arrangements for measuring the voltage across the thermistor are possible. As one example, the thermistor is connected as one element of a Wheatstone bridge. Alternatively, the thermistor may be coupled to a constant current supply or to a digital voltmeter.

Two thermistors are used to make measurements of effective thermal conductivity, thermal diffusivity and blood perfusion rate. One such thermistor is located at the measurement site and the second thermistor is located at a reference site, preferably approximately 0.5 inches from the measurement site. The thermistor circuit 51 (FIG. 1) heats the thermistor at the measurement site to a few degrees Celsius above the surrounding tissue (i.e., $\Delta T$), which surrounding tissue temperature is known from a temperature measurement made by the reference thermistor in the manner described above. The electrical energy, $\Gamma$, provided by the thermistor circuit 51 to the measurement site thermistor in order to maintain its temperature elevated by $\Delta T$ with respect to the surrounding tissue temperature is measured by the readout subsystem 42 or by the thermistor circuit itself.

A set of equations disclosed in an article entitled *The Simultaneous Measurement of, Thermal Conductivity, Thermal Diffusivity, and Perfusion in Small Volumes of Tissue.* (*Journal of Biomedical Engineering*, Valvano et al., August 1984, Vol. 106, pages 192–197), allows the effective tissue thermal conductivity to be computed according to the following equation:

$$K_{eff} = \frac{1}{\frac{3\Delta T}{\Gamma a^2} - \frac{1}{5K_b}} \quad (1)$$

where:
$\Delta T$=volume averaged temperature increase of the measurement thermistor relative to the surrounding tissue;
$\Gamma$=steady state power input provided by the thermistor circuit 51 to the measurement thermistor to maintain its temperature at $\Delta T$ above the surrounding tissue;
a=spherical radius of the cryoprobe; and
$K_b$=thermal conductivity of the thermistor.

The volume averaged temperature increase $\Delta T$ and the steady state power input $\Gamma$ are known from the thermistor circuit 51. The spherical probe radius a and the thermistor thermal conductivity $K_b$ may be specified by the probe manufacturer and/or measured. Thus, since $\Delta T$, $\Gamma$, a and $K_b$ are known values, the effective tissue thermal conductivity $K_{eff}$ can be computed according to the above equation (1).

Additional equations provided in the above-referenced article permit the effective tissue thermal conductivity to be used to compute blood perfusion rate and thermal diffusivity as follows:

$$\alpha_{eff} = \left| \frac{a}{\sqrt{\pi \beta / \Gamma \left[1 + \frac{K_m}{5K_b}\right]}} \right|^2 \quad (2)$$

$$w = \frac{(K_{eff} - K_m)^2}{K_m C_{bl} a^2} \quad (3)$$

where:
$\alpha_{eff}$=thermal diffusivity;
w=blood perfusion rate;

$K_m$=thermal conductivity of the tissue without blood flow;

β=slope of transient power input; and $C_{b1}$=blood specific heat.

Use of the equations (2) and (3) to compute the additional parameters of blood perfusion rate and thermal diffusivity may be desirable in generating the global tissue model, as will be described.

The effective tissue thermal conductivity is computed in response to measurements made with the thermistors 80a–80h (i.e., the effective tissue thermal conductivity is measured) prior to commencement of cryosurgery and the results of such "pre-surgery" measurements are used by the tissue model processor 40 to model thermal properties of the prostate tissue to be treated and by the prediction processor 36 to predict ice ball formation by the cryoprobes 18a–18n. Preferably, further measurements are made by the thermistors 80a–80h during the cryosurgical procedure. The results of such "surgery" measurements are used by the prediction processor 36 in order to verify the ice ball formation prediction, as will be described.

Figure 6:
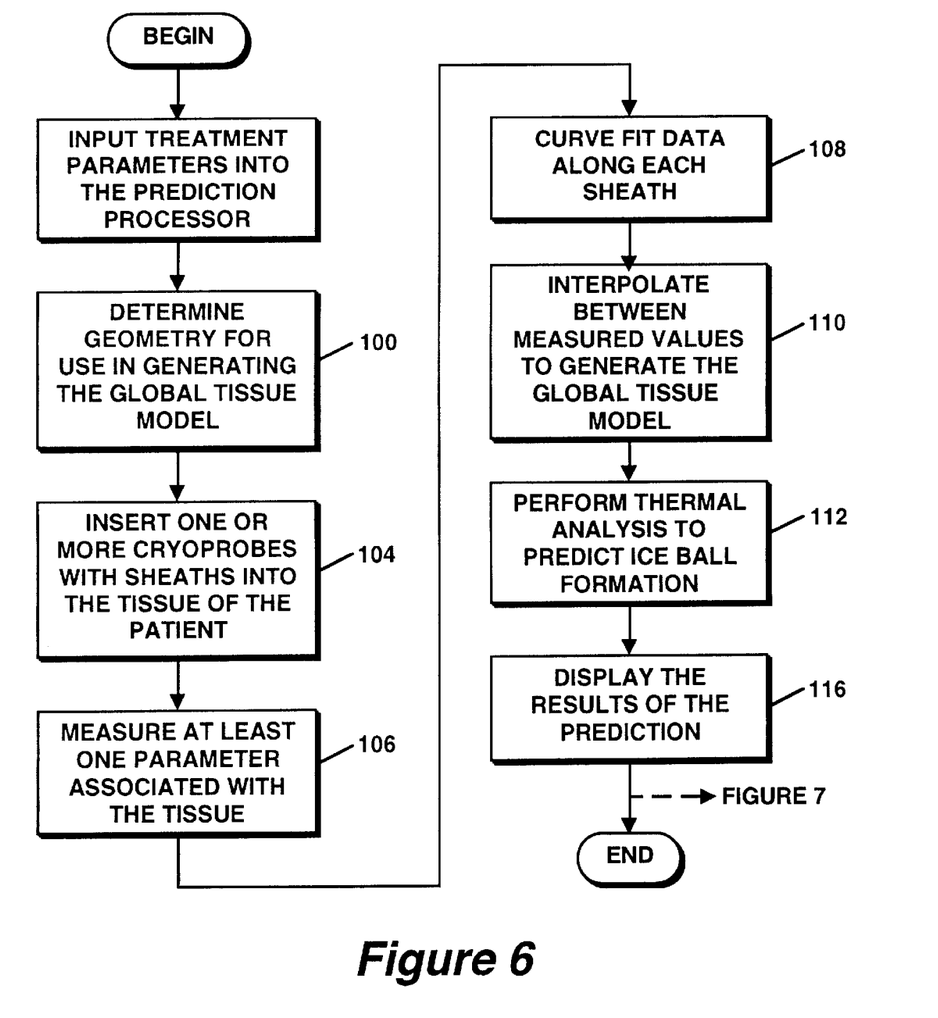
FIG. 6 is a flow diagram of an illustrative ice ball prediction method performed by the cryosurgical instrument of FIG. 1 prior to cryosurgery.

Referring to FIG. 6, an illustrative ice ball prediction method performed by the tissue model processor 40 and prediction processor 36 of the system 10 is shown. It will be appreciated by those of ordinary skill in the art that the particular sequence of steps shown in the flow diagrams contained herein is illustrative only and may be varied without departing from the spirit of the invention. Following commencement of the process, the operator of the system 10 enters various treatment parameters into the system in step 98 corresponding to intended aspects of the cryosurgical procedure to be carried out. Specifically, via the user interface 15 of the control unit 14, the operator, typically a physician, enters the intended relative position or placement of the probes 18a–18n (i.e., probe placement relative to other probes and relative to certain anatomical features), the depth of penetration of the probes, the duration of cryoprobe activation, the activation sequence of the probes, the de-activation time of each probe and the operational mode (e.g., a maximum freeze run starting at room temperature, with maximum freeze corresponding to a probe temperature on the order of –110° C. to –160° C., or a maximum freeze run starting at a –80° C. probe temperature). Various ways of describing the cryoprobe positions are possible. As one example, the locations of the cryoprobe tips in x, y, z space may be specified relative to a point in the prostate plus a vector along each cryoprobe if the cryoprobes are not in parallel. Alternatively, the x, y, z position of the cryoprobe tip(s) plus the x, y, z position of another known location on the cryoprobe(s) may be specified.

In step 100, the geometry of the region to be modelled by the tissue model processor 40 is defined. As will become apparent, the tissue model processor 40 is a computer program which is responsive to measurements of effective tissue thermal conductivity by the thermistors 80a–80h supported by the sheaths 22a–22n for interpolating the effective tissue thermal conductivity of the region under treatment, which includes the region between and around the cryoprobes 18a–18n. To this end, it is necessary that the tissue model processor 40 be provided with information regarding the geometry of the treated region (i.e., the geometry of the modelled region), including the placement of the cryoprobes relative to each other and to the location of certain anatomical features. More particularly, this information, which is input by the operator in step 98, is provided to the tissue model processor 40 in step 100.

In step 104, one or more cryoprobes 18a–18n with sheaths 22a–22n are inserted into the tissue of the patient targeted for cryosurgery in accordance with the treatment parameters entered in step 98. Specifically, the probes are inserted according to the placement and depth of penetration information entered in step 98.

The ultrasound probe 60 (FIG. 2) provides a two-dimensional image of the prostate to the physician to facilitate placement of the cryoprobes 18a–18n at the desired locations. The physician may guide the cryoprobes to the desired locations by eye (i.e., with use of the ultrasound image) or may use an adjustable guide block (not shown) which ensures a specific spacing between the probes. The cryoprobes 18a–18n are marked with depth indications, by which the physician determines when the specified depth of penetration has been reached.

Pre-surgery in-vivo measurements are made with one or more of the measuring devices 80a–80h supported by the cryoprobe sheaths 22a–22n in step 108. In one embodiment, the effective tissue thermal conductivity is measured at the eight locations of the thermistors 80a–80h on each of five cryoprobes 18a–18e inserted into the tissue in the manner described above (i.e., using thermistor measurements and equation (1)). Preferably, the thermal conductivity data collected in step 106 is curve fitted in step 108 in order to determine contour lines having substantially constant thermal conductivity characteristics within the modeled region. As one example, the measured data is plotted in x, y, z space and the data is examined to determine if the variation in measured effective thermal conductivity is small or insubstantial. If the variation is small, for example within a few percent over the prostate, then the thermal conductivity is assumed in the calculation to be constant throughout the entire prostate. However, if the variation is substantial, for example in the range of ten percent or more, then the data along each sheath is curve fitted, first with standard functions, such as exponentials, polynomials, etc., and the function providing the best fit is stored for each sheath.

The global tissue model, which is a characterization of the effective thermal conductivity of the tissue under treatment, is generated in step 110 by the tissue model processor 40 (FIG. 1). The global tissue model is generated in response to the geometry data determined in step 100 and the curve fitted measurement data derived in step 108. More particularly, in response to the measured effective thermal conductivity at the eight locations of the thermistors along each of five sheaths covering probes inserted into the patient, the relative placement of the sheaths and the geometry of the treated region, the effective thermal conductivity of the tissue around and between the sheaths is interpolated and stored in relation to each portion of the modelled region, thereby providing a distribution of effective thermal conductivity around and between the probes. Various interpolation schemes, including linear interpolation, are possible. As a further alternative, more than one interpolation scheme may be used and the results compared to generate the global tissue model. For prostates with significant measured variations in effective thermal conductivity, points having the same selected values of thermal conductivity along the sheaths may be identified by solving the functional relationships stored for each sheath. Equations may then be developed which describe the x, y, z contours of constant effective thermal conductivity in x, y, z space. These equations may then be used to assign a value of effective thermal conductivity to each x, y, z block in the SINDA calculation space.

It will be appreciated by those of ordinary skill in the art that the global tissue model may characterize additional thermal aspects of the treated tissue, including blood perfusion rate and thermal diffusivity. To this end, it may be desirable to compute thermal diffusivity and blood perfusion rate with equations (2) and (3) above, respectively, in response to thermistor measurements, to interpolate these parameters over the modelled region and combine the results with the effective tissue thermal conductivity in generating the global tissue model.

In step 112, the prediction processor 36 predicts the formation of ice balls in the prostate by calculating the expected temperature versus time history of the region. More particularly, the SINDA program of the prediction processor 36 breaks down the modelled region (which is defined by the user in step 98) into a plurality of blocks, some of which are occupied by probes according to the probe placement specified in step 98 and some of which represent tissue. The blocks can be arranged either two-dimensionally or three-dimensionally and each block is assigned a boundary value condition or equation, following which the temperature versus time history is calculated by computing the heat flow in each block.

The initial boundary value for blocks representing portions of a probe 18a–18n is set equal to the probe temperature measured prior to cryosurgery, in step 106, by the thermocouples 54a–54k or thermistors 80a–80h and input into the SINDA program in step 112. Thus, the probe temperature measurements are made once, prior to surgery, and preferably by the thermocouples 54a–54k. Another input to the SINDA program is the expected temperature time history of each cryoprobe which provides a boundary value equation assigned to each block representing a probe.

Blocks representing tissue are assigned a boundary value condition related to the effective thermal conductivity of the tissue. To this end, the global tissue model data provides the effective thermal conductivity to assign to the blocks representing tissue. Further, blocks corresponding to the urethra are assigned a boundary value condition according to the expected temperature of a warming fluid passed through the urethra. The urethra is maintained at nearly constant temperature during cryosurgery by a warmed catheter inserted into the urethra. The blocks in the SINDA program representing the catheter are assigned temperatures corresponding to a temperature that is set.

Additional inputs to the SINDA program include the treatment parameters entered in step 98, including placement of the probes relative to each other and to the treatment region, the activation sequence of the probes, the duration of the probe activation, the shutdown timing and sequence for the probes and the operational mode of the probes. In step 112, the prediction processor 36 computes a prediction of the formation of ice balls by each of the cryoprobes 18a–18n inserted into the prostate gland 50 in response to treatment parameters specified in step 98, the global tissue model and the results of the pre-surgery measurements made by the thermistors 80a–80h and/or thermocouples 54a–54k.

Figure 8:
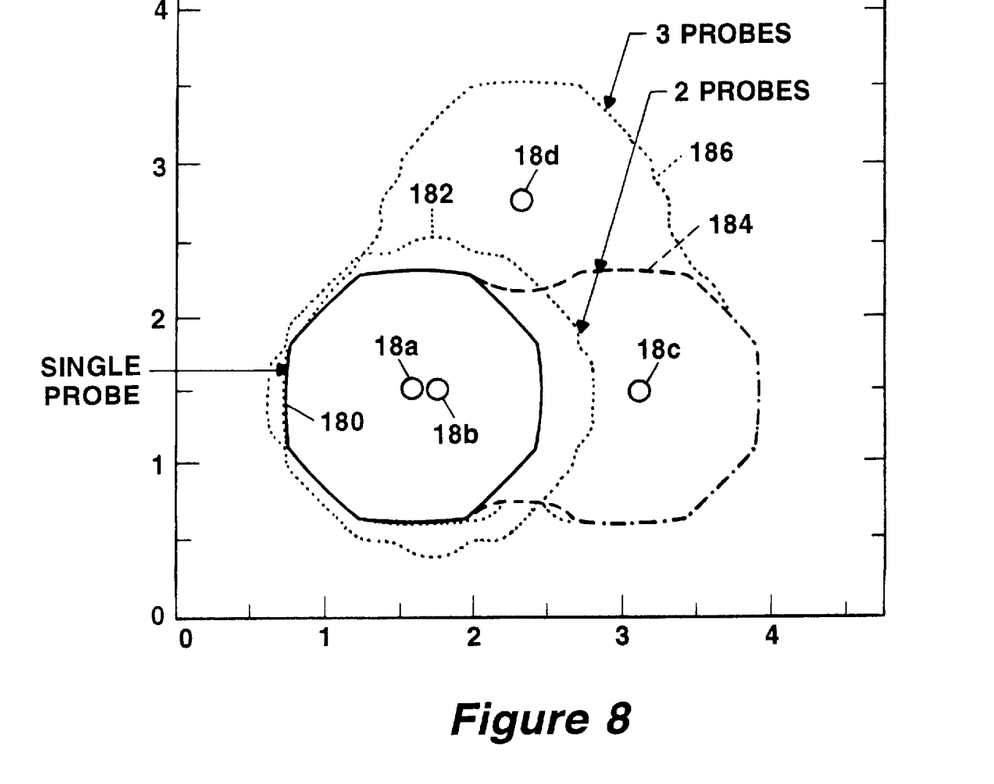
FIG. 8 shows an illustrative image of temperature contours in a prostate gland provided by the display of FIG. 1.

In step 116, contours of selected temperatures calculated by the prediction processor 36 are used to generate an image illustrating ice ball formation on the display 20. More particularly, the display 20 provides a representation of the temperature contours within the treated prostate gland as a result of activation of the cryoprobes 18a–18n. The displayed image may take various forms. In one embodiment, the display 20 provides a pictorial representation of the treated prostate gland with the temperature contours represented by boundary lines, as shown in FIG. 8.

Following completion of the process of FIG. 6, the operator, or physician, has information regarding precisely how the prostate gland 50 under treatment would be frozen upon activation of the cryoprobes 18a–18n in the specified manner. With this information, the physician is able to determine whether to proceed with, or alter the planned treatment routine in order to achieve an optimal area of freezing. For example, where the displayed ice ball prediction indicates an excessive area of freezing, the physician may alter the treatment routine by activating the cryoprobes 18a–18n for a shorter duration than otherwise planned. The physician may choose to modify the parameters of the treatment routine and repeat steps 98 through 116 in order to generate a new prediction of ice ball formation based on the modified treatment parameters.

Once the physician is satisfied with the displayed ice ball formation prediction, the pre-surgery prediction process of FIG. 6 is completed. The actual cryosurgery procedure may follow the process of FIG. 6 immediately or at some later time.

Figure 7:
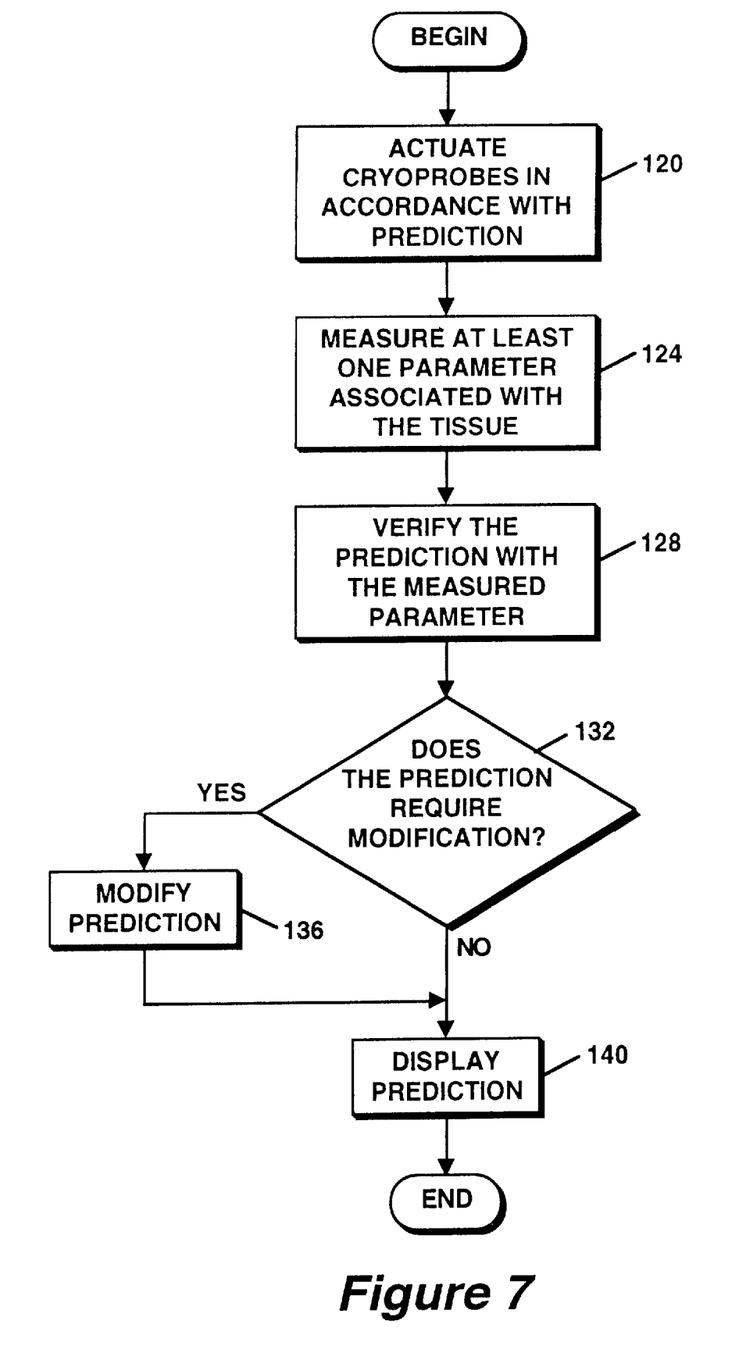
FIG. 7 is a flow diagram of an illustrative prediction verification method performed by the cryosurgical instrument of FIG. 1 during cryosurgery.

Referring to FIG. 7, the cryosurgical process commences in step 120, with activation of the cryoprobes 18a–18n. In step 124, at least one parameter associated with the tissue of the patient targeted for cryosurgery is measured by the measuring devices 80a–80h on the cryoprobe sheaths 22a–22n. These measurements are thus, performed during cryosurgery, when the cryoprobes are activated and thus, are referred to as "surgery" measurements.

In step 128, the ice ball formation prediction provided in step 112 of FIG. 6 is verified in response to the surgery measurements made in step 124, during cryosurgery. Prediction verification may be based on various surgery in-vivo measurements, including tissue temperature and impedance, since a correlation between the tissue impedance and ice ball size has been demonstrated. Thus, in the latter case, the measurement made in step 124 is a measurement of tissue impedance made with the impedance circuit 48 (FIG. 1) in the manner described above. More particularly, from measured laboratory data, it has been found that impedance and ice ball size can be related by a single curve when ice ball size is plotted against impedance. Therefore, impedance data measured at any time during cryosurgery may be converted to ice ball size simply by using this plotted relationship. Since the prediction model provides as one of its outputs the calculated size of the ice ball versus time, and the impedance measurements via the plotted relationship also provides a measurement of ice ball size versus time, a comparison between calculated results and results derived from impedance measurements allows the SINDA model predictions to be verified. Tissue temperature measurements may be made with either the thermocouples 54a–54k or thermistors 80a–80h in step 124 and the results used to verify the prediction. As one example, in cases where the prediction is based on temperature measurements made with the thermocouples 54a–54k, subsequent temperature measurements made with the thermistors 80a–80h in step 124 can be used to verify the thermocouple temperature measurements on which the prediction is based.

In step 132, it is determined whether the prediction generated in step 112 of FIG. 6 requires modification. As one example, if the ice ball prediction from step 112 differs from the prediction computed in response to measurements in step 128 by more than a predetermined amount, then the prediction is updated in step 136 and the updated prediction is displayed in step 140. Alternatively, if the ice ball formation prediction generated in step 112 of FIG. 6 does not differ from the prediction verification determined in step 128 by more than the predetermined amount, then the prediction generated in step 112 is subsequently displayed, in step 140. In this way, the physician is provided with a real time indication of ice ball formation, as the ice ball(s) are formed.

In certain applications, it may be desirable to repeat the prediction verification steps 124–140 at various times during the cryosurgical procedure. For example, the prediction may be verified periodically during the procedure. Alternatively, a first iteration of the prediction verification steps 124–140 may be based on in-vivo measurements of temperature made by thermocouples 54a–54k on each of the probes 18a–18n, a second iteration of steps 124–140 may be based on temperature measurements made by thermistors 80a–80h on each of the sheaths 22a–22n and a final iteration of steps 124–140 may be based on impedance measurements made by the thermistors. Alternatively, the prediction verification can be based on a combination of the measurements of the different parameters.

FIG. 8 shows an illustrative image provided on the display 20 (FIG. 1) and showing the prostate gland 50 having three cryoprobes 18a, 18b and 18c inserted therein. The boundary lines 180, 182, 184 and 186 around the cryoprobes 18a–18c indicate temperature contours within the prostate gland 50. Preferably, the temperature contours around the cryoprobes 18a–18n show different gradations of temperature, such as by different colors or line formats. In the illustrative display, boundary lines 180 and 182 indicate regions of 0° C. surrounding a single activated cryoprobe 18a and for two cryoprobes 18a and 18b spaced ⅛ inch apart, respectively. Boundary line 184 represents the 0° C. region around cryoprobes 18a and 18c in use with one inch between the cryoprobes and boundary line 186 represents the 0° C. region around three activated cryoprobes 18a, 18c, and 18d spaced one inch apart. The physician may select the cancer kill temperature contour to be highlighted by a special color.

It will be appreciated by those of ordinary skill in the art that the format of the image provided by the display may be readily varied while still providing the physician with the critical information regarding the cryosurgical process; namely, temperature contours in the treatment area. Further additional information may be readily displayed, including, as examples, patient information, measured prostate tissue properties, individual or multiple cryoprobe tip temperature histories and impedance data. The display 20 may additionally show the rectum and its location relative to the prostate gland and the cryoprobes.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. A cryosurgical instrument comprising:
   a cryoprobe adapted for being positioned in tissue of a patient targeted for cryosurgery and operative to form an ice ball upon activation;
   a sheath disposed over at least a portion of said cryoprobe, wherein said sheath is separable with respect to said cryoprobe; and
   at least one measuring device supported by said sheath for measuring a parameter of the tissue of the patient, wherein said parameter is selected from thermal conductivity and blood perfusion.

2. The instrument of claim 1 wherein said at least one measuring device is embedded in said sheath.

3. The instrument of claim 1 comprising a plurality of measuring devices supported by said sheath.

4. The instrument of claim 3 wherein said plurality of measuring devices are spaced axially and longitudinally along a portion of said sheath.

5. The instrument of claim 1 wherein the parameter of the tissue is selected from the group consisting of: temperature, thermal conductivity and blood perfusion.

6. A cryosurgical instrument comprising:
   a cryoprobe adapted for being positioned in tissue of a patient targeted for cryosurgry and operative to form an ice ball upon activation;
   a sheath disposed over at least a portion of said cryoprobe, wherein said sheath is separable with respect to said cryoprobe;
   at least one measuring device supported by said sheath for measuring a parameter of the tissue of the patient; and
   a processor for predicting prior to activation of said cryoprobe formation of said ice ball by said cryoprobe in the tissue of the patient over time in response to an output signal provided by said at least one measuring device.

7. The instrument of claim 6 further comprising a display for displaying said prediction of said formation of said ice ball.

8. The instrument of claim 1 wherein said at least one measuring device is a temperature measuring device providing a temperature output signal indicative of the temperature of the tissue of the patient following activation of said cryoprobe.

9. The instrument of claim 8 further comprising a processor for predicting formation of said ice ball by said cryoprobe in the tissue of the patient over time, wherein said processor is responsive to said temperature output signal for verifying said prediction.

10. The instrument of claim 1 wherein the tissue of the patient is the prostate gland.

11. An instrument for performing cryosurgery comprising:
    at least one cryoprobe adapted for being positioned in tissue of a patient and operative to form an ice ball upon activation;
    a processor for predicting prior to activation of said at least one cryoprobe formation of said ice ball by said at least one cryoprobe in the tissue of the patient over time; and
    at least one measuring device coupled to said processor for measuring a parameter of the tissue of the patient and for providing an output signal indicative of said parameter, wherein said processor is responsive to said output signal.

12. The instrument of claim 11 wherein said parameter is selected from the group consisting of: temperature, thermal conductivity and blood perfusion.

13. The instrument of claim 11 wherein said processor is further responsive to a model of the effective thermal conductivity of the tissue of the patient.

14. The instrument of claim 13 wherein the tissue of the patient is the prostate gland.

15. The instrument of claim 14 wherein said processor is further responsive to the effect of urethral warming.

16. The instrument of claim 11 wherein said at least one measuring device is operative to measure said parameter of the tissue of the patient following activation of said at least one cryoprobe and for providing an output signal indicative of said parameter, wherein said processor is responsive to said output signal for verifying said prediction.

17. The instrument of claim 11 comprising a plurality of cryoprobes adapted for being positioned in spaced relation in the tissue of the patient to form a respective plurality of ice balls upon activation, wherein said processor predicts formation of said plurality of ice balls by said plurality of cryoprobes in the tissue of the patient over time.

18. An instrument for performing cryosurgery comprising:
   a plurality of cryoprobes adapted for being positioned in spaced relation in tissue of a patient to form a respective plurality of ice balls upon activation;
   a processor for predicting formation of said plurality of ice balls by said plurality of cryoprobes in the tissue of the patient over time;
   at least one measuring device coupled to said processor for measuring a parameter of the tissue of the patient and for providing an output signal indicative of said parameter, wherein said processor is responsive to said output signal; and
   an impedance measurement circuit coupled to selected ones of said plurality of cryoprobes for providing an impedance output signal indicative of the impedance of the tissue of the patient and the size of the plurality of ice balls, wherein said processor is responsive to said impedance output signal for verifying said prediction, and wherein each of said plurality of cryoprobes has an electrically conductive tip portion and an electrically insulative portion adjacent to said tip portion.

19. The instrument of claim 11 further comprising a display for displaying said prediction of said formation of said ice ball.

20. A method of predicting formation of an ice ball by a cryoprobe in tissue of a patient targeted for cryosurgery, comprising the steps of:
   forming a model of the effective thermal conductivity of the tissue of the patient; and
   predicting the formation of the ice ball by the cryoprobe in the tissue of the patient based on said model and at least one measured parameter associated with the tissue of the patient.

21. A method of predicting formation of an ice ball by a cryoprobe in tissue of a patient targeted for cryosurgery, comprising the steps of:
   forming a model of the effective thermal conductivity of the prostate gland of the patient; and
   predicting the formation of the ice ball by the cryoprobe in the tissue of the patient based on said model and at least one measured parameter associated with the tissue of the patient.

22. The method of claim 21 wherein the ice ball formation predicting step includes predicting the formation of the ice ball as a function of urethral warming.

23. The method of claim 20 wherein said at least one parameter is selected from the group consisting of: temperature, thermal conductivity and blood perfusion.

24. A method of predicting formation of an ice ball by a cryoprobe in tissue of a patient targeted for cryosurgery, comprising the steps of:
   forming a model of the effective thermal conductivity of the tissue of the patient; and
   predicting the formation of the ice ball by the cryoprobe in the tissue of the patient based on said model and at least one measured parameter associated with the tissue of the patient, wherein said at least one parameter is temperature measured with at least one of a plurality of thermistors supported by a sheath covering a portion of the cryoprobe and a plurality of thermocouples disposed on the cryoprobe.

25. A cryosurgical instrument comprising:
   a cryoprobe adapted for being positioned in tissue of a patient targeted for cryosurgery and operative to form an ice ball upon activation;
   a sheath disposed over at least a portion of said cryoprobe, wherein said sheath is separable with respect to said cryoprobe; and
   at least one thermistor supported by said sheath for measuring a selected one of temperature, thermal conductivity, and blood perfusion of the tissue of the patient; and
   at least one thermocouple supported by said cryoprobe.

26. The instrument of claim 25 wherein said at least one thermocouple is a thin-film device.

* * * * *